United States Patent [19]

Collins et al.

[11] Patent Number: 5,094,111

[45] Date of Patent: Mar. 10, 1992

[54] THERMALLY INSULATED PIPELINE COATING TEST

[75] Inventors: Michael H. Collins; Alan R. Lyle, both of Chester, England

[73] Assignee: Shell Oil Company, Houston, Tex.

[21] Appl. No.: 698,348

[22] Filed: May 7, 1991

Related U.S. Application Data

[63] Continuation of Ser. No. 619,819, Nov. 29, 1990, abandoned, which is a continuation of Ser. No. 526,962, May 18, 1990, abandoned, which is a continuation of Ser. No. 247,829, Sep. 22, 1988, abandoned.

[30] Foreign Application Priority Data

Sep. 25, 1987 [GB] United Kingdom ................. 8722603

[51] Int. Cl.⁵ ............................................... G01N 3/08
[52] U.S. Cl. .................................... 73/834; 73/150 R
[58] Field of Search ................. 73/834, 760, 830, 835, 73/788, 150 R

[56] References Cited

U.S. PATENT DOCUMENTS

| | | | |
|---|---|---|---|
| 3,045,709 | 7/1962 | Rapp | 138/145 |
| 3,935,632 | 2/1976 | Maxson | 138/149 |
| 4,018,983 | 4/1977 | Pedlow | 138/177 |
| 4,273,806 | 6/1981 | Stechler | 427/119 |
| 4,393,901 | 7/1983 | Beck | 138/145 |
| 4,464,082 | 8/1984 | Isaacs | 138/32 |
| 4,660,861 | 4/1987 | Argy et al. | 138/149 |
| 4,744,842 | 5/1988 | Webster et al. | 138/DIG. 9 |

Primary Examiner—Jerry W. Myracle

[57] ABSTRACT

A method for determining the elongation before rupture of a syntactic material. The syntactic material consists of hollow microspheres in a polymer matrix material and may be used as insulation for deep water sub-sea flowlines, an application which requires that the material must be able to withstand a large tensile elongation without rupture. Elongation tests are performed in which various factors such as type of matrix and kind, size and bonding of microspheres are varied in order to determine the syntactic material providing maximum elongation without breaking.

3 Claims, 1 Drawing Sheet

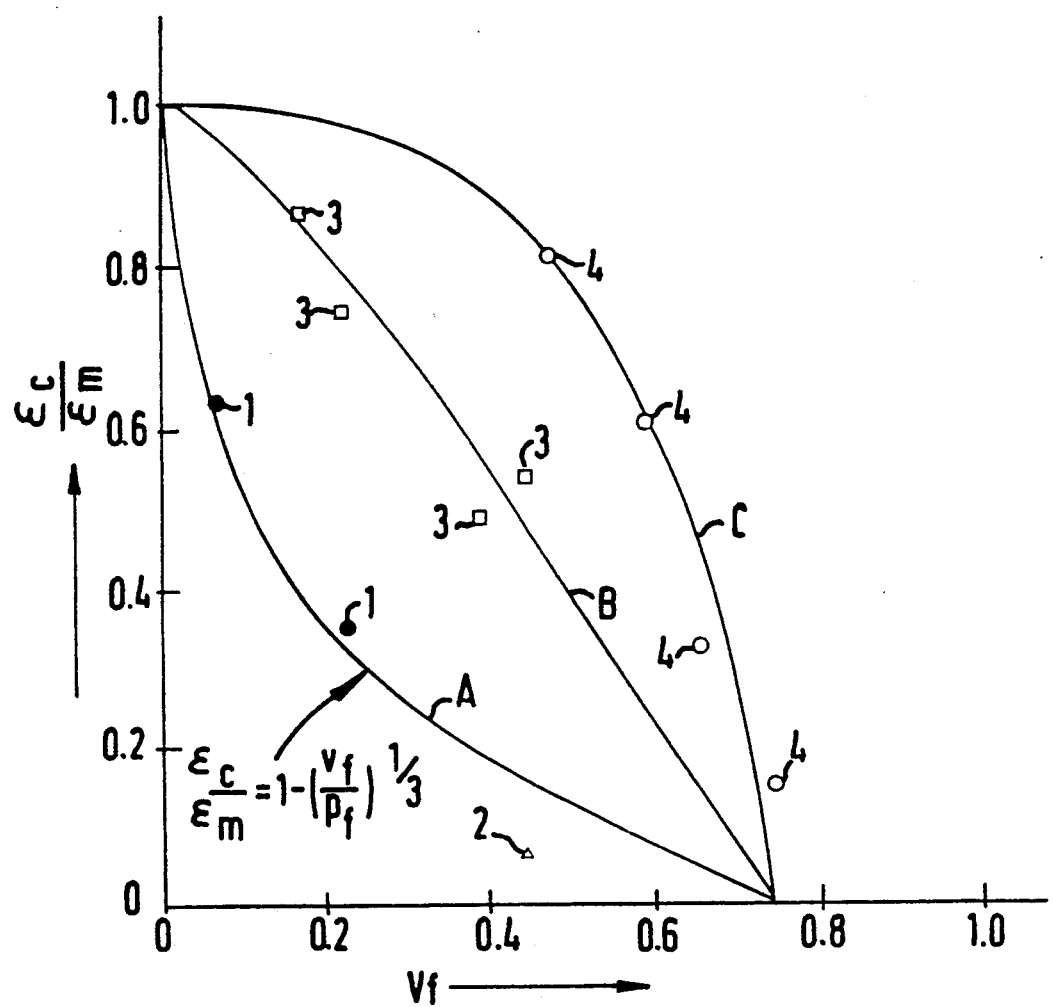

THERMALLY INSULATED PIPELINE COATING TEST

This is a division of application Ser. No. 07/619,819, filed Nov. 29, 1990, abandoned which is a continuation of application Ser. No. 07/562,962, filed May 18, 1990, abandoned, which is a continuation of application Ser. No. 07/247,829, filed Sept. 22, 1988, abandoned.

BACKGROUND OF THE INVENTION

The invention relates to a pipeline which is provided with a thermal insulation layer made of syntactic material. Syntactic material was initially developed as a buoyancy aid for deep-water submergence vehicles and consists of hollow microspheres in a polymeric matrix material. It has the advantage over foamed polymer in that it can, with the aid of high strength microspheres, be designed to withstand much greater hydrostatic pressures. The addition of the hollow microspheres also reduces the thermal conductivity of the material and therefore makes syntactic foam suitable for deeper water sub-sea flowline insulation.

In addition to having the necessary compressive strength and thermal conductivity, insulation for sub-sea flowlines must have adequate flexural performance to allow the coated pipe to be laid by any of the existing pipelaying methods including the use of a reel barge.

Hence the insulation material must be able to withstand a large tensile elongation without rupture.

It is known in the art that an increasing volume fraction of microspheres in the matrix material reduces the tensile stress at failure and that the mechanical strength of syntactic materials depends not only on the strength of the microspheres but also on their wettability with the resin. In view thereof, it has already been proposed to treat the microspheres with surface modification agents and to replace epoxide, polyurethane and polyester resins which are usually used as a matrix material by polyvinylchloride (PVC).

However, the tensile stress at failure of this existing syntactic material still requires improvement.

SUMMARY OF THE INVENTION

It is a purpose of the present invention to provide a thermally insulated pipeline of which the syntactic insulation layer has a higher elongation before rupture than any existing syntactic material.

In accordance with the invention this purpose is accomplished by a pipeline provided with a syntactic insulation layer comprising microspheres which are embedded in a matrix material made of polyolefin.

A preferred material for use as matrix material is polyproylene. Another suitable matrix material is polyethylene.

Laboratory experiments revealed that the presence of unbonded microspheres in polypropylene gives greater elongation before rupture than unbonded microspheres in PVC. A reason for the difference could be associated with the different rheological properites of the matrix materials. It is believed that under mechanical loads the flow process of semicrystalline polymers such as polypropylene and other polyolefins is different from that of amorphous PVC.

BRIEF DESCRIPTION OF THE DRAWING

The invention will now be explained in more detail with reference to the accompanying drawing which shows a comparison of the tensile elongation before rupture of various syntactic materials.

DESCRIPTION OF PREFERRED EMBODIMENT

More particularly, the drawing shows a plotted diagram in which the horizontal axis represents the volume fraction $V_f$ of microspheres in the matrix material and the vertical axis represents the ratio $\epsilon_c/\epsilon_m$ between the elongation before rupture of the syntactic material and the elongation before rupture of the pure matrix material.

The left line A represents a theoretical failure mode of syntactic materials comprising bonded microspheres. The middle line B represents the failure mode of syntactic material comprising unbonded microspheres in PVC. The right line C represents the failure mode of a syntactic material comprising unbonded microspheres in polypropylene.

As can be seen in the drawing the elongation before rupture of the syntactic material is influenced by the selection of the matrix material and the bond of the microspheres to the matrix material.

Studies on the failure processing polymers at or near rigid spherical inclusions show three distinct types of failures (i) detachment from the spheres, (ii) cohesive failure in the polymer near the poles of isolated spheres and (iii) cohesive failure in the polymer midway between two spheres in close proximity and with their centers in the line of applied stress. The cavity produced by (iii) grows at right angle to the applied stress and leads to a catastrophic rupture of the specimen whereas cavities and debonds formed at the poles of isolated spheres grow in the direction of the applied stress and do not lead directly to rupture.

In practice, since the volume concentration of microspheres in syntactic materials generally is about 50%, there are no isolated spheres and failure is likely to take place either through debonding or through cohesive failure in the polymer midway between spheres. An approximate relationship for failure in the matrix material is given by:

$$\frac{\epsilon_c}{\epsilon_m} = 1 - \frac{V_f^{\frac{1}{3}}}{P_f} \quad (1)$$

where $\epsilon_c$ and $\epsilon_m$ are the elongation at break of the syntactic and matrix material respectively. $V_f$ and $P_f$ are the volume fraction of filler and the packing fraction of the filler at maximum filler concentration respectively. In the derivation of (1) the effect of, for example, Poisson's ratio, the glass transition temperature $T_G$ of the matrix and the shape factor of the filler are not taken into account. It is assumed also that the adhesion of the matrix to the filler is good.

Line A in the drawing shows a plot in accordance with equation (1) of $\epsilon_c/\epsilon_m$ as in function of $V_f$ and includes experimental results on systems with a good bond between the spheres and the matrix materials. Points 1 are plotted experimental results of the failure of a syntactic material consisting of bonded microspheres in PVC. Point 2 is the plotted experimental result of the failure of a sytactic material consisting of bonded microspheres in polyester. The agreement between theory and experiment is reasonably good and shows that equation (1) can be used to predict elongation at break for systems where the failure is in the matrix. The drawing also includes experimental results for systems with a poor bond between the glass spheres and the matrix material. For these the elongation is much greater then predicted by equation (1) and this is to be expected since the polymer is free to flow around the filler. Points 3 are plotted experimental results of the failure of a syntactic material consisting of unbonded microspheres in PVC and points 4 are plotted experimental results of the failure of a syntactic material consisting of unbonded microspheres in polypropylene. Lines B and C are interpolations of the plotted experimental results.

As can be seen in the drawing unbonded spheres in polypropylene (line C) give greater elongation than unbonded spheres in PVC (line B). The reasons for the difference could be associated with the rheological properties of the matrices; the flow processes of semicrystalline polymers such as polypropylene are considered to be different from those of amorphous PVC.

As the rheological properties of other polyolefins, such as polyethylene, are similar to those of polypropylene the same large elongation before failure should be true for these semicrystallines polymers.

The tests further revealed that failure of the matrix material under tensile load was frequently initiated adjacent to large size microspheres and furthermore that utilization of small size microspheres had a positive effect on the thermal insulation properties because of the absence of free convection of the gas filling such small size microspheres. It was found that utilization of microspheres having a maximum diameter less than about 100 μm (micrometers) had a positive effect on both the mechanical strength and thermal insulation properties of the syntactic material and that utilization of microspheres having a maximum diameter less than about 60 μm created a further improvement of these physical properties of the syntactic material.

What is claimed is:

1. A method for comparing the elongation before breaking of different syntactic materials, each material comprising a selected polymer matrix with selected filler microspheres dispersed therein, comprising the steps of:

a) determining 1) the elongation at break ($\epsilon_m$) of the polymer matrix, and 2) the packing fraction ($P_f$) of the filler microspheres;

b) varying the volume fraction ($V_f$) of the filler microspheres in a plurality of syntactic samples and determining the elongation at break ($\epsilon_c$) of each sample;

c) calculating the relationship for failure in the polymer matrix by the formula:

$$\frac{\epsilon_c}{\epsilon_m} = 1 - \frac{V_f}{P_f};$$

d) generating a curve for $\epsilon_c/\epsilon_m$ versus $V_f$ for the plurality of syntactic samples which shows the parameter of elongation at break of the selected polymer matrix as $V_f$ is varied;

e) generating at least one other curve by repeating steps a-d for a different syntactic material reflecting at least one of 1) a different polymer matrix, and 2) different filler microspheres which are different as to at least one of i) kind, ii) sizing, and iii) bonding; and f) comparing the curves to determine the syntactic material providing maximum elongation without breaking.

2. The method of claim 1 wherein at least one selected polymer matrix comprises microspheres embedded in a matrix material of polyolefin, the maximum diameter of the microspheres being about 60 μm.

3. The method of claim 1 wherein at least one selected polymer matrix comprises microspheres embedded in a matrix material of polyolefin, the maximum diameter of the microspheres being about 100 μm.

* * * * *